United States Patent [19]
Walther et al.

[11] Patent Number: 5,422,353
[45] Date of Patent: Jun. 6, 1995

[54] TETRAHYDROPYRIDINE DERIVATIVES

[75] Inventors: Gerhard Walther, Bingen; Karl-Heinz Weber, Gau-Algesheim; Werner Stransky, Gau-Algesheim; Franz J. Kuhn, Gau-Algesheim; Erich Lehr, Waldalgesheim; Enzio Müller, Ingelheim am Rhein; Günter Schingnitz, Bad Kreuznach; Helmut Ensinger, Ingelheim am Rhein, all of Germany

[73] Assignee: Boehringer Ingelheim KG, Ingelheim am Rhein, Germany

[21] Appl. No.: 145,264

[22] Filed: Oct. 29, 1993

Related U.S. Application Data

[63] Continuation of Ser. No. 838,961, Feb. 21, 1992, abandoned, which is a continuation of Ser. No. 505,210, Apr. 4, 1990, abandoned, which is a continuation of Ser. No. 299,299, Jan. 23, 1989, abandoned.

[30] Foreign Application Priority Data

Jan. 21, 1988 [DE] Germany .................. 38 01 659.1

[51] Int. Cl.$^6$ .................. A61K 31/435; A61K 31/44; C07D 211/70; C07D 211/82
[52] U.S. Cl. .................. 514/277; 514/358; 546/340; 546/347
[58] Field of Search .............. 546/340, 347; 514/277, 514/358

[56] References Cited

PUBLICATIONS

L. G. Wade, Jr. "Organic Chemistry," p. 349, Prentice-Hall Inc. Publishers 1987.
Burger, "Medicinal Chemistry" Second Edition, p. 497 Interscience Publishers, Inc 1960.

*Primary Examiner*—Alan L. Rotman
*Attorney, Agent, or Firm*—D. E. Frankhouser; A. R. Stempel; M-E. M. Devlin

[57] ABSTRACT

The invention relates to new tetrahydropyridine derivatives, processes for preparing them and their use as pharmaceutical compositions with cholinomimetic properties.

7 Claims, No Drawings

TETRAHYDROPYRIDINE DERIVATIVES

This is a continuation of application Ser. No. 07/838,961, filed Feb. 21, 1992, abandoned, which is a continuation of application Ser. No. 07/505,210, filed Apr. 4, 1990, (abandoned), which is a continuation of application Ser. No. 07/299,299, filed Jan. 23, 1989, (abandoned).

The invention relates to tetrahydropyridine derivatives, to processes for preparing them and their use as pharmaceutical compositions.

We have found that the compounds of the invention are suitable for the treatment of diseases caused by restricted function of the cholinergic system, for example, Alzheimer's disease, senile dementia, and also for peripheral use, e.g. in treating glaucoma.

According to one aspect of the invention, we provide compounds of formula I

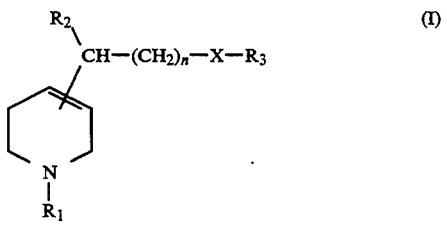

(I)

wherein $R_1$ represents a hydrogen atom, a branched or unbranched ($C_{1-3}$)-alkyl group, an allyl group or a propargyl group;

$R_2$ represents a hydrogen atom or a methyl group;

$R_3$ represents a branched or unbranched ($C_{1-4}$)-alkyl group, an allyl group or a propargyl group;

X represents oxygen or sulphur; and n represents one of the integers 0 and 1, the compounds existing either as racemates or as individual optical isomers or mixtures thereof, and acid addition salts and quaternary derivatives thereof, with the proviso that, if $R_1$ and $R_3$ represent methyl, $R_2$ is hydrogen, X is oxygen and n is 1, the substituent cannot be in the para-position relative to the nitrogen for a compound in the form of its free base.

Preferred compounds of the invention are those wherein $R_1$ represents a methyl group, $R_2$ represent a hydrogen atom, $R_3$ represents a methyl, ethyl or n-propyl group and n is 0.

Other preferred compounds of the invention are those wherein the 4-position is substituted.

Preferred quaternary derivatives of compounds of the invention have formula Ia

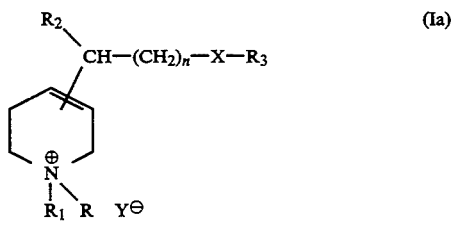

(Ia)

wherein $R_2$, $R_3$, X and n are defined as hereinabove, $R_1$ is as defined above other than a hydrogen atom, R represents a methyl or ethyl group, $Y^\ominus$ represents an anion, preferably a halide.

Examples of alkyl groups with 1 to 4 carbon atoms include, inter alia, methyl, ethyl, n-propyl, isopropyl, n-butyl, sec.-butyl and isobutyl. The halogen may be fluorine, chlorine, bromine or iodine.

The compound 4-(methoxyethyl)-1-methyl-1,2,3,6-tetrahydropyridine is known (Chem. Abs. 68 P 105106s), but hitherto its use as a pharmaceutical or in any composition has not bee described or suggested.

The compounds of formula I may be prepared analogously to known processes. According to a further aspect of the invention, we provide a process for preparing compounds of formula I as defined hereinbefore wherein a pyridine derivative of formula IV

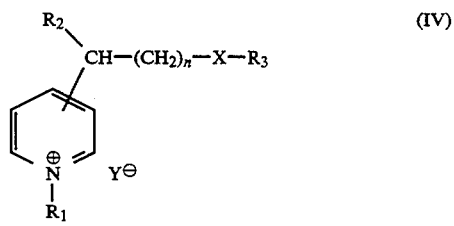

(IV)

(wherein $R_1$, $R_2$, $R_3$, X and n are as defined hereinbefore and $Y^\ominus$ is an anion) is reduced with a complex metal hydride, followed, where it is desired to prepare a compound of formula I or Ia wherein $R_1$ represents hydrogen, by demethylation of a corresponding compound of formula I wherein $R_1$ represents methyl followed, if desired, by resolution of any mixture of compounds into individual optical isomers thereof, and conversion of any compound of formula I into an acid addition salt or quaternary derivative thereof.

Compounds of formula I wherein $R_1$ is other than hydrogen may thus be synthesised according to the following reaction plan.

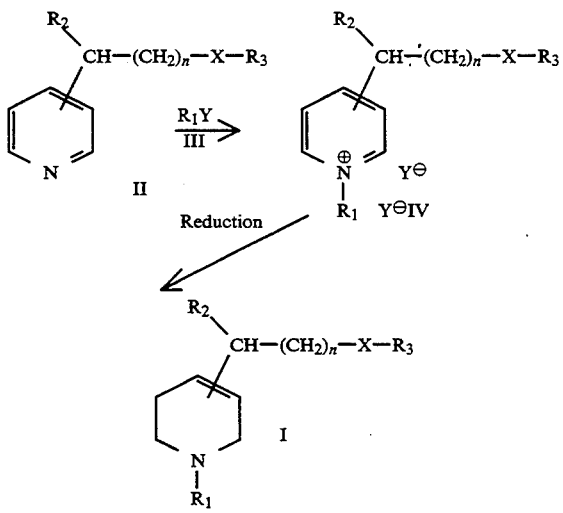

Starting from pyridine derivatives of formula I wherein n, X, $R_2$ and $R_3$ are defined as hereinbefore, these derivatives being either known or prepared by analogous methods, N-alkylation is carried out using an alkylating agent of formula $R_1Y$ (wherein $R_1$ is defined as hereinbefore and Y is a suitable anion) for example by reacting with the corresponding a) alkylhalides, particularly alkylbromides or alkyliodides
b) esters of alkyl- or arylsulphonic acid, particularly esters of methane- or p-toluene-sulphonic acid
c) sulphuric acid esters, e.g. dimethylsulphate in a solvent such as acetone, acetonitrile, toluene or ethanol, at temperatures between ambient temperature and the boiling point of the reaction mixture.

The reduction of the quaternary compounds of formula IV to yield the compounds of formula I may also be carried out by known methods, e.g. using complex metal hydrides (e.g. Andor Hajos, Komplexe Hydride, VEB Deutscher Verlag der Wissenschaften, Berlin 1966, page 208 and 431), such as sodium borohydride, in suitable solvents; the reaction is preferably carried out with sodium borohydride in alcohols such as methanol or ethanol at 0°–25° C.

Compounds of formula I wherein $R_1$ represents a hydrogen atom are obtained by demethylation of compounds of formula I in which $R_1$ represents a methyl group e.g by reacting phosgene in toluene and subsequent hydrolysis of the N-chlorocarbonyl compounds formed as intermediates (R. Banholzer et al., Arzneimittelforschung 35 (I), 217–228 (1985)).

The quaternary compounds of formula Ia may be prepared analogously to the quaternary salts IV by reacting compounds of formula I with alkylating reagents.

The compounds of formulae I and Ia have valuable pharmacological properties. Thus, in bonding studies, they show affinities with muscarinic receptors and muscarbin-agonistic GTP-shifts (GTP=guanosintriphosphate). (Birdshall, N. I. M., E. C. Hulme and J. M. Stockton 1984 in T.I.P.S. Supplement, Proc. Internat. Symposium on Subtypes of Muscarinic Receptors, Ed. Hirschowitz, Hammer, Giacchetti, Keirns, Levine; Elsevier p. 4–8).

The receptor binding studies were carried out according to: A. Closse, H. Bittiger, D. Langenegger and A. Wanner, Naunyn-Schmiedeberg's Arch. Pharmacol. 335, 372–377 (1987). The results are shown in Table A.

TABLE A

| Receptor binding studies | |
|---|---|
| Radioligand: | L(+)cis-[2-methyl-$^3$H]-N,N,N-trimethyl-1,3-dioxolan-4-methanammonium-iodide NET-647, Messrs. NEN (New England Nuclear; DU PONT). |
| Organ: | Cerebral cortex (rat) |

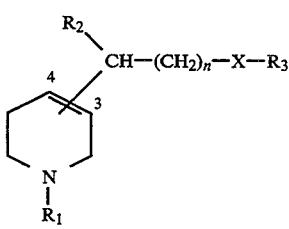

(I)

| Example | $R_1$ | $R_2$ | $R_3$ | n | Subst. Pos. | X | Ki [nmol/l] |
|---|---|---|---|---|---|---|---|
| 1 MA | —CH$_3$ | —H | —CH$_3$ | 0 | 4 | —O— | 337 |
| 2 MA | —CH$_3$ | —H | —C$_2$H$_5$ | 0 | 4 | —O— | 210 |
| 9 MA | —CH$_3$ | —H | -n-C$_3$H$_7$ | 0 | 4 | —O— | 140 |
| 13 MA | —CH$_3$ | —H | —CH$_3$ | 0 | 4 | —S— | 15 |
| 4 MA | —CH$_3$ | —H | —C$_2$H$_5$ | 0 | 4 | —S— | 8.3 |
| 19 OX | —CH$_3$ | —H | —C$_2$H$_5$ | 0 | 3 | —S— | 690 |

TABLE A-continued

| Receptor binding studies | | | | | | | |
|---|---|---|---|---|---|---|---|
| OX | —CH$_3$ | —H | —CH$_3$ | 1 | 4 | —O— | 3900 |

MA = maleate, OX = oxalate

In pharmacological test models, a cholinergic activity was demonstrated both in vitro and in vivo. Thus, for example, 4-methoxymethyl-1-methyl-1,2,3,6-tetrahydropyridine and 4-ethoxymethyl-1-methyl-1,2,3,6-tetrahydropyridine administered in a dosage of 1 mg/kg and 3 mg/kg i.v. and 1-methyl-4-methylthiomethyl-1,2,3,6-tetrahydro-pyridine administered in a dosage of 0.1 mg/kg and 0.3 mg/kg i.v., exhibit an arousal reaction typical of cholinomimetics in the EEG (electroencephalograph) of a conscious rabbit.

Being muscarinic agonists (cholinomimetics) the substances are suitable for the treatment of diseases caused by restricted function of the cholinergic system.

In view of the pharmacological findings the compounds are suitable, for example, for treating the following diseases: Alzheimer's disease, senile dementia and cognitive disorders and the compounds may also be used to improve memory.

Quaternary derivatives of formula Ia are particularly suitable for peripheral use, e.g. for the treatment of glaucoma.

The compounds of the invention may be used on their own or combined with other active substances according to the invention, optionally combined with other pharmacologically active substances, e.g. other cerebroactivators. Pharmaceutical compositions comprising compounds of the invention and including the compound excluded by the proviso above in admixture with a pharmaceutically acceptable carrier, diluent or excipient comprise a further aspect of the invention. Suitable forms for administration include tablets, capsules, suppositories, solutions, syrups, emulsions or dispersible powders.

According to a further aspect, the invention provides the use of a compound of the invention, including the compound excluded by the proviso above, for the preparation of a pharmaceutical composition with a cholinomimetic activity.

According to a yet further aspect, the invention provides a method of treatment of conditions caused by restricted function of the cholinergic system in a human or non-human animal body, which comprises administering to said body an effective amount of a compound of the invention, including the compound excluded by the proviso above.

Tablets may be made for example by mixing the active substance or substances with known excipients, such as inert diluents, e.g. calcium carbonate, calcium phosphate or lactose, disintegrants such as corn starch or alginic acid, binders such as starch or gelatine, lubricants such as magnesium stearate or talc, and/or agents for obtaining delayed release such as carboxymethylcellulose, cellulose acetate phthalate, or polyvinylacetate. The tablets may also consist of several layers.

Coated tablets may be prepared in an analogous manner by coating cores produced in the same way as the tablets with agents normally used for coating tablets, such as collidone or shellac, gum arabic, talc, titanium dioxide or sugar. To obtain delayed release or avoid incompatabilities the core may also consist of several layers. Similarly, the tablet coating may consist of several layers in order to obtain delayed release, whilst the excipients mentioned for the tablets above may be used.

Syrups containing the active substances or combinations of active substances according to the invention may additionally contain a sweetener such as saccharin, cyclamate, glycerol or sugar and a flavour enhancer, e.g. a flavouring such as vanillin or orange extract. They may also contain suspension adjuvants or thickeners such as sodium carboxymethylcellulose, wetting agents, e.g. condensation products of fatty alcohols with ethylene oxide, or preservatives such as p-hydroxybenzoates.

Injection solutions are prepared in the usual way, e.g. with the addition of preservatives such as p-hydroxybenzoates or stabilisers such as alkali metal salts of ethylenediamine tetraacetic acid and transferred into injection vials or ampoules.

Capsules containing one or more active substances or combinations of active substances may be prepared, for example, by mixing the active substances with inert carriers such as lactose or sorbitol and packing them into gelatin capsules.

Suitable suppositories may be prepared, for example, by mixing with carriers provided for this purpose such as neutral fats or polyethyleneglycol or derivatives thereof.

The therapeutically active single dose for a human body is generally in the range from 1 to 100 mg.

The Examples which follow are intended to illustrate the invention without restricting its scope:

EXAMPLES OF PHARMACEUTICAL FORMULATIONS

| A) Tablets | per tablet |
|---|---|
| Active substance | 80 mg |
| Lactose | 140 mg |
| Corn starch | 240 mg |
| Polyvinylpyrrolidone | 15 mg |
| Magnesium stearate | 5 mg |
| | 480 mg |

The finely ground active substance, lactose and some of the corn starch are mixed together. The mixture is screened, then moistened with a solution of polyvinylpyrrolidone in water, kneaded, granulated whilst moist and dried. The granules, the remaining corn starch and magnesium stearate are screened and mixed together. The mixture is compressed to form tablets of suitable shape and size.

| B) Tablets | per tablet |
|---|---|
| Active substance | 60 mg |
| Corn starch | 190 mg |
| Lactose | 55 mg |
| Microcrystalline cellulose | 35 mg |
| Polyvinylpyrrolidone | 15 mg |
| Sodium carboxymethyl starch | 23 mg |
| Magnesium stearate | 2 mg |
| | 380 mg |

The finely ground active substance, some of the corn starch, lactose, microcrystalline cellulose and polyvinylpyrrolidone are mixed together, the mixture is screened and processed with the remaining corn starch and water to form granules which are dried and screened. The sodium carboxymethyl starch and the magnesium stearate are added, a mixture is formed and compressed to produce tablets of suitable size.

| C) Ampoules | |
|---|---|
| Active substance | 50 mg |
| Sodium chloride | 10 mg |
| Doubly distilled water q.s. ad | 1.0 ml |

PREPARATION

The active substance and sodium chloride are dissolved in doubly distilled water and the solution is transferred into ampoules under sterile conditions.

| D) Drops | |
|---|---|
| Active substance | 5.0 g |
| Methyl p-hydroxybenzoate | 0.1 g |
| Propyl p-hydroxybenzoate | 0.1 g |
| Demineralised water q.s. ad | 100.0 ml |

PREPARATION

The active substance and preservatives are dissolved in demineralised water and the solution is filtered and transferred into 100 ml vials.

EXAMPLE 1

4-Methoxymethyl-1-methyl-1,2,3,6-tetrahydropyridine a) 4-Methoxymethyl-1-methyl-pyridinium iodide A solution of 4.8 g (0.039 mol) of 4-methoxymethyl-pyridine in 25 ml of acetonitrile is mixed with 6.6 g (0.047 mol) of methyl iodide and stirred for 5 hours at ambient temperature. Then the partially precipitated quaternary salt is precipitated by the addition of ethyl acetate. 9.1 g (88% of theory) of 4-methoxymethyl-1-methyl-pyridinium iodide are obtained, m.p. 105°–108° C.

The analytically pure methoiodide has a melting point of 106°–108° C. (CH$_3$CN).

[C$_8$H$_{12}$NO]+I− (265.10).

Calculated: C 36.25; H 4.57; H 5.28; I 47.87; Found: 36.02, 4.60, 5.26, 47.69.

b) 13.15 g (0.348 mol) of sodium borohydride are added in batches, with stirring, at 10°–15° C., to a solution of 38.4 g (0.145 mol) of 4-methoxymethyl-1-methyl-pyridinium iodide in 380 ml of methanol. The reaction mixture is then stirred for a further 2 hours at ambient temperature, acidified with 2N hydrochloric acid and evaporated in vacuo. The residue is combined with 40% aqueous potassium carbonate solution and extracted with ether. The oil remaining when the organic phase is dried over anhydrous sodium sulphate is distilled.

Yield: 17.6 g, colourless oil (86% of theory); b.p. 70°–72° C./20 mbar.

$^1$H NMR (CDCl$_3$; 90 MHz) 5.65 (m,1H,CH=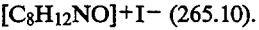); 3.85(m,2H,O—CH$_2$); 3.32 (s,3H,OCH$_3$); 2.95 (m,2H,NCH$_2$); 2.50(m,2H,NCH$_3$); 2.33(s,3H,NCH$_3$); 2.18(m,2H,CH$_2$—C=).

The corresponding 4-methoxymethyl-1-methyl-1,2,3,6-tetrahydro-pyridine maleate (1:1) has a melting point of 86°–87° C. (ethyl acetate).

EXAMPLE 2

4-Ethoxymethyl-1-methyl-1,2,3,6-tetrahydropyridine

A solution of 5.9 g (0.043 mol) of 4-ethoxymethyl-pyridine and 7.33 g (0.052 mol) of methyl iodide in 50 ml of acetonitrile is stirred for 14 hours at ambient temperature. The reaction mixture is then evaporated down in vacuo. The residue (12.1 g) is dissolved in 120 ml of methanol and reduced analogously to Example 1 b) with 3.94 g of sodium borohydride.

Yield: 4.7 g (70% of theory); b.p. 82°–83° C./20 mbar. 4.7 g of 4-ethoxymethyl-1-methyl-1,2,3,6-tetrahydropyridine and 3.5 g of maleic acid are dissolved in ethyl acetate with heating. When the solution cools, 4.7 g of the maleate are obtained (m.p. 88°–89° C.).

$C_9H_{17}NO \times C_4H_4O_4$ (271.32).

Calculated: C 57.55; H 7.80; N 5.16; Found: 57.71, 7.62, 5.09.

Citrate: m.p. 124°–126° C. (acetonitrile) $C_9H_{17}NO \times C_6H_8O_7$ (347.37).

EXAMPLE 3

1-Ethyl-4-methoxymethyl-1,2,3,6-tetrahydropyridine 6.5 g (0.053 mol) of 4-methoxymethyl pyridine and 9.9 g of ethyl iodide are refluxed in 65 ml of acetonitrile for 1 hour. After the solvent has been distilled off the quaternary salt remaining is taken up in methanol and reduced with sodium borohydride analogously to Example 1 b). 7.8 g (95.2% of theory) of the title compound are obtained (b.p. 85° C./20 mbar).

The corresponding maleate has a melting point of 85°–87° C. (ethyl acetate).

$C_9H_{17}NO \times C_4H_4O_4$ (271.32).

Calculated: C 57.55; H 7.80; N 5.16; Found: 57.50, 7.83, 5.31.

EXAMPLE 4

4-[(Ethylthio)methyl]-1-methyl-1,2,3,6-tetrahydropyridine 8.2 g (0.054 mol) of 4-[(ethylthio)methyl]pyridine are dissolved in 60 ml of acetonitrile and then 9.1 g of methyliodide are added. After 12 hours the reaction mixture is evaporated down in vacuo. The residue is reacted analogously to Example 1 b) with sodium borohydride in methanol and worked up. The crude product obtained is distilled (5.2 g; 56.3% of theory; b.p. 118°–120° C./20 mbar) and then chromatographed on neutral aluminium oxide using chloroform as eluant. 4.4 g of 4-[(ethylthio)methyl]-1-methyl-1,2,3,6-tetrahydropyridine are obtained, which is converted with one equivalent of maleic acid into the maleate (m.p. 102°–105° C., from ethyl acetate).

$C_9H_{17}NS \times C_4H_4O_4$ (237.39).

Calculated: C 54.33; H 7.37; N 4.87; S 11.16; Found: 54.25, 7.13, 4.95, 11.08.

EXAMPLE 5

3-Methoxymethyl-1-methyl-1,2,5,6-tetrahydropyridine 17.8 g (0.067 mol) of 3-methoxymethyl-1-methylpyridinium iodide (m.p. 57°–59° C./isopropanol) are reduced analogously to Example 1 b) with 6.1 g (0.16 mol) of sodium borohydride in methanol. The crude product is distilled under reduced pressure (b.p. 63°–73° C./20 mbar) and then purified by column chromatography ($Al_2O_3$/ethyl acetate).

$^1H$ NMR (CDCl$_3$; 400 MHz) 5.76 (m,1H,CH=); 3.85 (s,2H,O—CH$_2$); 3.29 (s,3H,OCH$_3$); 2.90 (m,2H,NCH$_2$); 2.49 (m,2H,NCH$_2$); 2.37 (s,3H,NCH$_3$); 2.21 (m,2H,CH$_2$—C=).

The maleic acid salt has a melting point of 62°–64° C. (ethyl acetate/ether).

$C_8H_{15}NO \times C_4H_4O_4$ (257.29).

Calculated: C 56.02; H 7.44; N 5.44; Found: 55.86, 7.67, 5.57.

EXAMPLE 6

1,1-Dimethyl-4-methoxymethyl-1,2,3,6-tetrahydropyridinium bromide 6.8 g (0.072 mol) of methyl bromide in 30 ml of acetonitrile are added dropwise to a solution of 5.1 g (0.036 mol) of 4-methoxymethyl-1-methyl-1,2,3,6-tetrahydropyridine in 50 ml of acetonitrile.

After 1 hour, the methobromide obtained is suction filtered and recrystallised from acetonitrile.

Yield: 4.8 g (56.3% of theory); m.p. 139°–142° C. (acetonitrile).

$[C_9H_{18}NO]^+Br^-$ (236.17).

Calculated: C 45.77; H 7.68; N 5.93; Br 33.84; Found: 45.66, 7.55, 5.77, 33.72.

The following compounds are obtained by analogous processes:

EXAMPLE 7

1,1-Dimethyl-4-[(ethylthio)methyl]-1,2,3,6-tetrahydropyridinium iodide

M.p. 132°–133° C. (acetonitrile).

Calculated: C 38.34; H 6.44; N 4.47; S 10.24; Found 38.64, 6.68, 4.48, 10.23.

EXAMPLE 8

4-Methoxymethyl-1,2,3,6-tetrahydropyridine

Fumarate: m.p. 115°–117° C. (methanol/ether). $C_7H_{13}NO \times C_4H_4O_4$ (243.27).

Calculated: C 54.31; H 7.04; N 5.76; Found: 54.15, 6.87, 5.72.

$^1H$ NMR (CD$_3$OD; 90 MHz) 6.75 (s,2H,Fu); 5.82 (m,1H,CH=); 3.87 (m,2H,OCH$_2$); 3.72 (m,2H,NCH$_2$); 3.32 (m,2H,NCH$_2$); 3.31 (s,3H,OCH$_3$); 2.30 (m,2H,CH$_2$—C=).

EXAMPLE 9

1-Methyl-4-propoxymethyl-1,2,3,6-tetrahydropyridine

B.p. 103°–104° C./20 mbar; maleate: m.p. 89°–91° C. (ethyl acetate/ether).

$C_{10}H_{19}NO \times C_4H_4O_4$ (285.35).

Calculated: C 58.93; H 8.12; N 4.91; Found: 58.98, 8.10, 4.89.

EXAMPLE 10

4-Allyloxymethyl-1-methyl-1,2,3,6-tetrahydropyridine

B.p. 103° C./30 mbar; fumarate: m.p. 86°–88° C. (acetonitrile).

$C_{10}H_{17}NO \times 1.5 \, C_4H_4O_4$ (341.37).

Calculated: C 56.30; H 6.79; N 4.10; Found: 56.03, 6.86, 4.28.

EXAMPLE 11

4-Isopropoxymethyl-1-methyl-1,2,3,6-tetrahydropyridine

B.p. 90°–91° C./20 mbar; maleate; m.p. 108°–109° C. (ethyl acetate).

$C_{10}H_{19}NO \times C_4H_4O_4$ (285.35).

Calculated: C 58.93; H 8.12; N 4.91; Found: 58.76, 8.09, 4.90.

EXAMPLE 12

4-[1-(Methoxy)ethyl]-1-methyl-1,2,3,6-tetrahydropyridine

B.p. 76°–78° C./30 mbar; fumarate: m.p. 94°–96° C. (acetone).
$C_9H_{17}NO \times C_4H_4O_4$ (271.32).
Calculated: C 57.55; H 7.80; N 5.16; Found: 57.62, 7.94, 5.10.

EXAMPLE 13

1-Methyl-4-[(methylthio)methyl]-1,2,3,6-tetrahydropyridine

B.p. 105°–106° C./20 mbar; maleate: m.p. 82°–85° C. (ethyl acetate).
$^1H$ NMR (CD$_3$OD; 400 MHz).
5.28 (s,2H,Ma); 5.65 (m,1H,CH=); 3.82 (m,2H,NCH$_2$); 3.43 (m,2H,NCH$_2$); 3.10 (s,2H,SCH$_2$); 2.96 (s,3H,N—CH$_3$); 2.58 (m,2H,CH$_2$—C=); 2.00 (s,3H,SCH$_3$).

EXAMPLE 14

1-Methyl-4-[(propylthio)methyl]-1,2,3,6-tetrahydropyridine

B.p. 127°–128° C./20 mbar; oxalate: m.p. 152°–154° C. (acetonitrile).
$C_{10}H_{19}NS \times C_2H_2O_4$ (275.37).
Calculated: C 52.34; H 7.69; N 5.09; S 11.64; Found: 52.82, 7.87, 5.21, 11.65.

EXAMPLE 15

1-Ethyl-4-[(ethylthio)methyl]-1,2,3,6-tetrahydropyridine

B.p. 125°–126° C./30 mbar; oxalate: m.p. 132°–134° C. (acetonitrile).
$C_{10}H_{19}NS \times C_2H_2O_4$ (275.37).
Calculated: C 52.34; H 7.69; N 5.09; S 11.64; Found: 52.61, 7.89, 5.24, 11.55.

EXAMPLE 16

3-[(Ethylthio)methyl]-1-methyl-1,2,5,6-tetrahydropyridine oxalate

M.p. 116°–117° C. (methanol/ether).
$C_9H_{17}NS \times C_2H_2O_4$ (261.35).
Calculated: C 50.55; H 7.33; N 5.36; S 12.27; Found: 50.34, 7.33, 5.58, 12.21.

EXAMPLE 17

1-Methyl-4-[(methylthio)ethyl]-1,2,3,6-tetrahydropyridine

B.p. 121°–122° C./20 mbar; oxalate: m.p. 110°–112° C. (acetonitrile).
$C_9H_{17}NS \times C_2H_2O_4$ (261.35).
Calculated: C 50.55; H 7.33; N 5.36; S 12.27; Found: 50.46, 7.48, 5.45, 12.31.

EXAMPLE 18

1-Methyl-4-[1-(methylthio)ethyl]-1,2,3,6-tetrahydropyridine

B.p. 104°–106° C./20 mbar; oxalate: m.p. 134°–136° C. (acetonitrile).
$C_9H_{17}NS \times C_2H_2O_4$ (261.35).

Calculated: C 50.55; H 7.33; N 5.36; S 12.27; Found: 50.74, 7.46, 5.50, 12.19.

EXAMPLE 19

3-[(Methylthio)methyl]-1-methyl-1,2,5,6-tetrahydropyridine oxalate

M.p. 119°–121° C. (acetonitrile/ethyl acetate).
$C_8H_{15}NS \times C_2H_2O_4$ (247.32).
Calculated: C 48.56; H 6.93; N 5.66; S 12.97; Found: 48.45, 6.97, 5.64, 13.03.

PREPARATION OF STARTING COMPOUNDS

The following examples illustrate possible methods of synthesising the starting compounds of formula II.

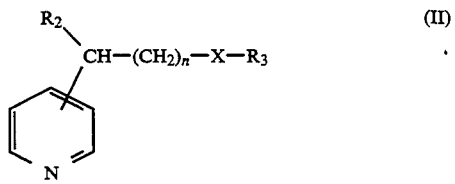

(i). 4-[1-(Methoxy)ethyl]-pyridine

A solution of 8.4 g (0.068 mol) of 4-(1-hydroxyethyl)-pyridine in 20 ml of absolute tetrahydrofuran is added dropwise to a suspension of 2 g (0.083 mol) of sodium hydride (3.3 g of 60% oil dispersion; washed in toluene) in 80 ml of absolute tetrahydrofuran. After the development of hydrogen has ceased, 23 g (0.16 mol) of methyliodide are added at 18°–20° C. and the mixture is left to react for 2 hours. The reaction mixture is concentrated by evaporation, the residue is combined with 40% aqueous potassium carbonate solution and extracted with ether. The organic phase is separated, dried over sodium sulphate and concentrated by evaporation. After distillation of the crude product at 82°–85° C./20 mbar, 5.2 g (55.6% of theory) of the title compound are obtained.

(ii). 4-(Isopropoxymethyl)-pyridine 3.4 g of sodium are dissolved in 120 ml of isopropanol and 11 g (0.067 mol) of 4-chloromethylpyridine-hydrochloride are added. The reaction mixture is refluxed for 10 hours under nitrogen, with stirring, then after cooling it is made weakly acidic with dilute hydrochloric acid and concentrated by evaporation under reduced pressure. The residue is made alkaline with 40% potassium carbonate solution and extracted with ether. After drying with anhydrous sodium sulphate the organic phase is concentrated by evaporation. The crude product is then distilled.

Yield: 5 g (49.3% of theory).
B.p. 95°–97° C./20 mbar.

(iii). 4-[(Ethylthio)methyl]-pyridine

A solution of 19 g (0.28 mol) of sodium ethoxide in 200 ml of absolute ethanol is combined with 8.7 g (0.14 mol) of ethylmercaptane and stirred for 15 minutes at ambient temperature. Then 23 g (0.14 mol) of 4-(chloromethyl)-pyridine hydrochloride are added. After a reaction period of 3 hours the mixture is made weakly acidic with 2N hydrochloric acid, the solvent is distilled off, the residue is made alkaline with 40% potassium carbonate solution and extracted with ether. The organic phase is dried over anhydrous sodium sulphate and concentrated by evaporation. When the residue is subjected to vacuum distillation 17.4 g (81% of theory) of 4-[(ethylthio)methyl]-pyridine are obtained.

B.p. 122°-123° C./20 mbar.

(iv). 4-[2-(Methylthio)ethyl]-pyridine

To a solution of 13.6 g (0.2 mol) of sodium ethoxide in 150 ml of absolute ethanol are added 23 g (0.165 mol) of 4-mercaptoethylpyridine [See L. Bauer and L. A. Gardella, Jr., J. Org. Chem. 26, 82 (1961)] and after 15 minutes at 15°-18° C. 28.1 g (0.2 mol) of methyl iodide are added dropwise.

The reaction mixture is stirred for 30 minutes at ambient temperature, made weakly acidic with 2N hydrochloric acid and evaporated down in vacuo. The residue is made alkaline with 40% potassium carbonate solution and extracted with ether. After drying over anhydrous sodium sulphate the organic phase is evaporated down the residual oil is distilled in vacuo.

B.p. 133°-134° C./20 mbar.

(v). 4-[1-(Methylthio)ethyl]-pyridine

This compound is obtained analogously to Example III from 4-(1-chloroethyl)-pyridine (see DE-OS 3 334 937 A 1) and sodium thiomethoxide.

B.p. 113°-116° C./20 mbar.

TABLE 1

Tabular summary of the Examples

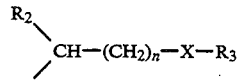
(I)

| Example | $R_1$ | $R_2$ | $R_3$ | n | Subst. Pos. | X |
|---|---|---|---|---|---|---|
| 1 | —CH₃ | —H | —CH₃ | 0 | 4 | O |
| 2 | —CH₃ | —H | —C₂H₅ | 0 | 4 | O |
| 3 | —C₂H₅ | —H | —CH₃ | 0 | 4 | O |
| 4 | —CH₃ | —H | —C₂H₅ | 0 | 4 | S |
| 5 | —CH₃ | —H | —CH₃ | 0 | 3 | O |
| 8 | —H | —H | —CH₃ | 0 | 4 | O |
| 9 | —CH₃ | —H | -n-C₃H₇ | 0 | 4 | O |
| 10 | —CH₃ | —H | —CH₂—CH=CH₂ | 0 | 4 | O |
| 11 | —CH₃ | —H | —CH(CH₃)₂ | 0 | 4 | O |
| 12 | —CH₃ | —CH₃ | —CH₃ | 0 | 4 | O |
| 13 | —CH₃ | —H | —CH₃ | 0 | 4 | S |
| 14 | —CH₃ | —H | -n-C₃H₇ | 0 | 4 | S |
| 15 | —C₂H₅ | —H | —C₂H₅ | 0 | 4 | S |
| 16 | —CH₃ | —H | —C₂H₅ | 0 | 3 | S |
| 17 | —CH₃ | —H | —CH₃ | 1 | 4 | S |
| 18 | —CH₃ | —CH₃ | —CH₃ | 0 | 4 | S |
| 19 | —CH₃ | —H | —CH₃ | 0 | 3 | S |

TABLE 2

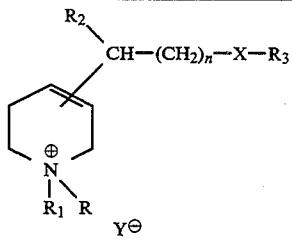
(Ia)

| Example | $R_1$ | $R_2$ | $R_3$ | R | Y | n | Subst. Pos. | X |
|---|---|---|---|---|---|---|---|---|
| 6 | —CH₃ | —H | —CH₃ | —CH₃ | —Br | 0 | 4 | O |
| 7 | —CH₃ | —H | —C₂H₅ | —CH₃ | —I | 0 | 4 | S |

What is claimed is:

1. A tetrahydropyridine derivative of formula

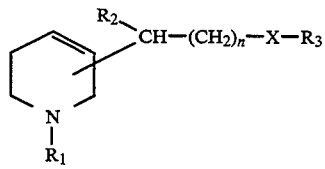
(I)

wherein $R_1$ is hydrogen, branched or unbranched $C_1$-$C_3$ alkyl, an allyl group or a propargyl group;

$R_2$ is hydrogen or methyl $R_3$ is branched or unbranched $C_1$-$C_4$ alkyl, an allyl group or a propargyl group;

X is oxygen or sulphur; and n is an integer of 0 or 1, the racemate or the optically active compound, a pharmaceutically acceptable salt thereof, with the proviso that, in the case of the free base, if $R_1$ and $R_3$ are methyl, $R_2$ is hydrogen, X is oxygen and n is 1, the substituent cannot be in the para-position relative to the nitrogen.

2. The tetrahydropyridine derivative as recited in claim 1, wherein $R_1$ is methyl, $R_2$ is hydrogen, $R_3$ is methyl, ethyl or n-propyl and n is 0.

3. The tetrahydropyridine derivative as recited in claim 1 wherein $$\overset{R_2}{\underset{}{\diagdown}}\!CH\!-\!(CH_2)_n\!-\!X\!-\!R_3$$

is in the 4-position.

4. A tetrahydropyridine quaternary derivative of formula

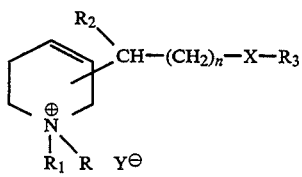
(Ia)

wherein $R_1$ is branched or unbranched $C_1$-$C_3$ alkyl, an allyl group or a propargyl group;

$R_2$ is hydrogen or methyl $R_3$ is branched or unbranched $C_1$-$C_4$ alkyl, an allyl group or a propargyl group;
X is oxygen or sulphur;
n is an integer 0 or 1;
R is methyl or ethyl; and
Y is an anion.

5. The tetrahydropyridine derivative as recited in claim 4 wherein Y is a halogen.

6. A pharmaceutical composition of matter comprising an effective amount of a tetrahydropyridine derivative of formula

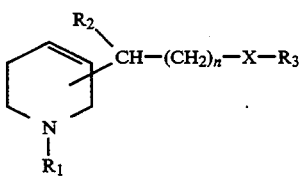

wherein
$R_1$ is hydrogen, branched or unbranched $C_1$-$C_3$ alkyl, an allyl group or a propargyl group;
$R_2$ is hydrogen or methyl;
$R_3$ is branched or unbranched $C_1$-$C_4$ alkyl, an allyl group or a propargyl group;
X is oxygen or sulphur; and
n is an integer 0 or 1;
the racemate or the optionally active compound, the acid addition salt or the quaternary derivative thereof,
and a pharmacologically acceptable carrier.

7. A method for treating diseases in warm-blooded animals caused by restricted function of the cholinergic system comprising administering to said animal a therapeutically effective amount of a tetrahydropyridine derivative of formula

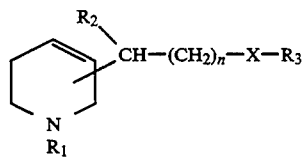 (Ia)

wherein
$R_1$ is hydrogen, branched or unbranched $C_1$-$C_3$ alkyl, an allyl group or a propargyl group;
$R_2$ is hydrogen or methyl,
$R_3$ is branched or unbranched $C_1$-$C_4$ alkyl, an allyl group or a propargyl group;
X is oxygen or sulphur; and
n is an integer 0 or 1;
the racemate or the optically active compound, a pharmaceutically acceptable salt thereof.

* * * * *